United States Patent [19]

Guinovart et al.

[11] Patent Number: 5,595,763
[45] Date of Patent: Jan. 21, 1997

[54] TUNGSTEN (VI) COMPOSITIONS FOR THE ORAL TREATMENT OF DIABETES MELLITUS

[75] Inventors: Joan J. Guinovart, Esplugues de Llobregat; Albert Barberà, Barcelona; Joan E. Rodríguez-Gil, Avinyó, all of Spain

[73] Assignee: Quimica Farmaceutica Bayer S.A., Barcelona, Spain

[21] Appl. No.: 504,020

[22] Filed: Jul. 19, 1995

[51] Int. Cl.$^6$ .......................... A61K 33/24; A61K 31/28
[52] U.S. Cl. ............................................. 424/617; 514/492
[58] Field of Search ............................ 424/617; 514/492

[56] References Cited

U.S. PATENT DOCUMENTS

| | | | |
|---|---|---|---|
| 4,746,504 | 5/1988 | Nimrod et al. | 424/1.1 |
| 4,851,430 | 7/1989 | Kopf-Maier et al. | 514/502 |
| 4,882,171 | 11/1989 | Posner et al. | 424/616 |
| 5,374,537 | 12/1994 | Orlando et al. | 435/29 |

OTHER PUBLICATIONS

Insulin–Like Action of Tungstate in Diabetic Rats, Albert Barbera, et al, Aug. 5, 1994, Journal of Biological Chemistry, vol. 269, No. 31.

Diabetes, vol. 43, Oct. 1994, "Reply to Domingo, et al and McNeill, et al".

Encyclopedia of Chemical Technology, 3rd Edition, vol. 23, Kirk Othmer "Tungsten Compounds", pp. 426, 435 & 438, 1983.

Toxicology, 66 (1991), pp. 279–287, J. L. Domingo, et al, "Oral Vanadium Administration to Streptozotocindiabetic Rats . . .".

Endeavour, New Series, vol. 17, No. 1, 1993, Schechter, et al, "Vanadium Salts and the Future Treatment of Diabetes".

Archives of Biochemistry and Biophysics, vol. 301, No. 2, 1993, pp. 411–415, Joan Enric Rodriguez-Gil, et al.

Diabetes, vol. 40, Dec. 1991, pp. 1675–1678, McNeill, et al, "Insulinlike Effects of Sodium Selenate in Streptozocin–Induced Diabetic Rats".

Science, vol. 227, pp. 1474–1477, Heyliger, et al, "Effect of Vanadate on Elevated Blood Glucose and Depressed Cardiac Performance of Diabetic Rats" (1985).

*Primary Examiner*—Raymond Henley, III
*Attorney, Agent, or Firm*—Michael J. Striker

[57] ABSTRACT

The pharmaceutical composition contains an effective amount of a tungsten (VI) compound, preferably a tungstate or a isopolytungstate, and more preferably sodium tungstate. In the method of lowering blood sugar in a human suffering from type I or type II diabetes mellitus, an effective amount of the composition is administered orally. Compared with the known vanadium compositions, the invention has the advantage of providing a similar high sugar-lowering activity but with a much lower oral toxicity at effective doses, both short- and long-term. Compared with insulin, the invention does not present the adverse effect of inducing hypoglycemia when administered in excess.

17 Claims, 2 Drawing Sheets

TUNGSTEN (VI) COMPOSITIONS FOR THE ORAL TREATMENT OF DIABETES MELLITUS

BACKGROUND OF THE INVENTION

This invention relates to a pharmaceutical composition comprising a tungsten (VI) compound for use as an insulin mimicker, and to a method of lowering blood sugar in a mammal using the pharmaceutical composition.

Diabetes mellitus is a major global health problem which is recognised by the World Health Organisation to be reaching epidemic proportions. It is now the fourth leading cause of death in most developed countries and a disease that is increasing rapidly in countries undergoing industrialisation. Estimates of worldwide diabetes prevalence have increased from 30 million in 1985 to more than 100 million in 1994. Diabetes mellitus is a disease caused by defective carbohydrate metabolism and characterized by abnormally large amounts of sugar glucose in the blood and urine. Diabetes mellitus can eventually damage the eyes, kidneys, heart, and limbs, and can endanger pregnancy.

Diabetes mellitus is usually classified into two types. Type 1, or insulin-dependent diabetes mellitus (IDDM), formerly called juvenile-onset diabetes, which occurs in children and young adults, has been implicated as one of the autoimmune diseases. Rapid in onset and progress, it accounts for about 10 to 15 percent of all cases. Type 2, or non-insulin-dependent diabetes mellitus (NIDDM), formerly called adult-onset diabetes, is usually found in persons over 40 years old and progresses slowly. Often it is not accompanied by clinical illness in its initial stages and is detected instead by elevated blood or urine glucose levels.

Diabetes is considered a group of disorders with multiple causes, rather than a single disorder. The human pancreas secretes a hormone called insulin that facilitates the entry of the sugar glucose into tissues of the body and its utilization, thus providing energy for bodily activities. In a person with diabetes, however, the entry of glucose is impaired, a result either of a deficiency in the amount of insulin produced or of altered target cells. Consequently, sugar builds up in the blood and is excreted in the urine. In the Type 1 diabetic, the problem is almost always a severe or total reduction in insulin production. In the Type 2 diabetic, the pancreas often makes a considerable quantity of insulin, but the hormone is unable to promote the utilization of glucose by tissues.

With adequate treatment most diabetics maintain blood-sugar levels within a normal or nearly normal range. This enables them to live normal lives and prevents some long-term consequences of the disease. For the Type 1 diabetic with little or no insulin production, therapy involves insulin injections. For Type 2 diabetics, most of whom are at least moderately overweight, the basics of therapy are diet control, weight reduction, and exercise. Weight reduction appears to partially reverse the condition of insulin resistance in the tissues. If a patient's blood-sugar level is still high, the physician may add insulin injections.

Besides the discomfort associated with its administration by injection, the problem of controlling the dose of insulin also exists. The hypoglycemia produced by an insulin overdose, depending on its importance, may lead to tremulousness, cold sweat, piloerection, hypothermia, and headache, accompanied by confusion, hallucinations, bizarre behaviour, and ultimately, convulsions and coma. Therefore, it would be very advantageous to have an insulin substitute not producing hypoglycemia in case of accidental overdose.

Given that insulin is only active when administered by injection, and that the administered dose must be controlled, it has been clearly stated for years that an oral active insulin-substitute, especially if it does not produce hypoglycemia of overdose, would greatly decrease diabetic patients' discomfort and risk.

Unfortunately, so far the therapeutical problem of having an adequate oral treatment of diabetes mellitus is still unsolved. In recent years, several inorganic compounds have been described which mimic the effects of insulin, both in vivo and in isolated cells and tissues. These include some vanadium compounds (cf. Heyliger et al., "Effect of vanadate on elevated blood glucose and depressed cardiac performance of diabetic rats", *Science* 1985, vol. 227, pp. 1474–7); selenate (cf. McNeill et al., "Insulinlike effects of sodium selenate in streptozotrocin-induced diabetic rats", *Diabetes* 1991, vol. 40, pp. 1675–8), and lithium salts (cf. Rodriguez-Gil el al., "Lithium restores glycogen synthesis from glucose in hepatocytes from diabetic rats", *Arch. Biochem. Biophys.* 1993, vol. 301, pp. 411–5). From all these vanadium, selenium and lithium compounds, so far, only vanadium compounds have been proposed as insulin-mimicker drugs for the oral treatment of diabetes (cf. Schechter et al., "Vanadium salts and the future treatment of diabetes", *Endeavour* 1993, vol. 17, pp. 27–31). The vanadium derivatives which have been studied as insulin-mimickers include: alkaline earth metal or alkaline metal vanadate (vanadium in its +5 oxidation state combined with oxygen, especially orthovanadate $VO_4^{3-}$), vanadyl $VO^{2+}$ salts and peroxovanadium complexes (cf. U.S. Pat. No. 4,882,171).

Vanadium compounds are currently undergoing clinical trials in Europe and America. But oral administration of vanadium compounds has the drawback of toxicity at effective doses. Administered concentrations must be close to the toxic level, if the insulin-mimetic effects in animals are to be achieved. Vanadium-treatment is always accompanied by marked negative side effects that are independent of the chemical form of vanadium used (cf. Domingo et al., "Oral vanadium administration to streptozocin-diabetic rats has marked negative side-effects wich are independent of the form of vanadium used", *Toxicology* 1991, vol. 66, pp. 279–87.). Remarkable signs of vanadium compounds toxicity are observed at all the doses that are able to lower blood glucose, including a significant mortality rate. In summary, clinical trials of vanadium compounds have been criticized on the grounds of the high toxicity at therapeutical doses, up to the point that some authors have claimed that vanadium is not a viable option to treat human diabetes. A recent letter to *Diabetes* (1994, vol. 43, p. 1270), stated that "With the possible exception of cytotoxic drugs, it must be almost unprecedented for an agent with such an impressive record of morbidity and mortality to reach the point of being tested in humans."

In summary, so far there is no satisfactory solution to the problem of having an insulin-mimicker drug for oral treatment of diabetes mellitus. To be pharmaceutically acceptable, such a drug simultaneously must have a high sugar-lowering activity and a low oral toxicity at effective doses. Toxicity must be low not only short-term but also long-term, because diabetes mellitus is a chronic disease. It would be very advantageous also, that the drug does not produce hypoglycemia in case of accidental overdose, which is a problem of the administration of insulin by injection.

SUMMARY OF INVENTION

It has been found that oral administration of tungsten (VI) compounds is surprisingly as effective as the known administration of vanadium compounds in normalizing blood glucose levels, both in IDDM (Type 1 diabetes) and NIDDM (Type 2 diabetes).

Besides, and equally important, it has been found that, contrary to what is known for vanadium compounds and to what was expected in general for tungsten compounds, the tungsten (VI) compounds of the present invention are virtually inocuous at effective doses, both short-term and long-term, and they do not produce hypoglycemia in case of overdose.

Many uses of tungsten (VI) compounds were previously known in industry: catalysts, reagents, pigments, corrosion inhibitors, fire inhibitors, in antifreeze solutions, in the manufacture of lasers, etc. But no therapeutic use of any tungsten (VI) compound has ever been disclosed or suggested. On the contrary, such a use would have been considered unlike because soluble tungsten compounds, in general, have been considered toxic materials, both by injection and orally. Thus, for instance, the $LD_{50}$ of sodium tungstate, $Na_2WO_4.2H_2O$, was estimated in 140–160 mg/kg when injected subcutaneously in rats. It was also known that guinea pigs treated orally or intravenously with sodium tungstate suffered anorexia, colic, incoordination of movement, trembling, and dyspnea. Besides, orally in rats, the toxicity of sodium tungstate was higher than the one corresponding to other tested tungsten (VI) compounds (cf. Kirk-Othmer, "Encyclopedia of Chemical Technology", 1983, 3rd. ed., vol. 23, p. 435, and references therein).

According to the toxicological information available for tungsten (VI) compounds, in particular for sodium tungstate, a therapeutic use of these compounds, especially in a human chronic disease, is unexpected. But, surprisingly, it has been found that:

i) The $LD_{50}$ for sodium tungstate when administrated orally to Wistar rats is 3922 mg/kg. Using the same protocol the value obtained for the oral administration of sodium vanadate, $NaVO_3$, is 98 mg/kg. This means that, orally administered, tungstate is 40 times less toxic that vanadate; and also that tungstate is about 30 times less toxic orally than by injection.

ii) At high doses, vanadate treatment induces diarrhea, convulsions, and blood in the feces. However, none of these symptoms is observed when animals are treated with tungstate at doses used in the experiment (up to 8000 mg/kg).

iii) When tungstate experiments are run in parallel with vanadate, the mortality of rats treated with vanadate is much higher (about 60%) than among tungstate treated rats in which case mortality is similar to untreated diabetic controls (about 10%).

iv) No toxicological effects are observed in healthy rats treated with therapeutical doses of sodium tungstate for 8 months.

v) From toxicological studies using human cells cultured in vitro, it has been concluded that tungstate at the level found in blood of treated animals is well below the concentrations found to be toxic for cultured human muscle or liver cells. This surprising result indicates that tungstate can be used in humans at pharmacologically effective doses with no risk of damage to liver or muscle tissues.

On the other hand, taking into consideration the strong differences in chemical behavior between vanadium and tungsten, it was unexpected that tungsten (VI) compounds would have an activity as insulin-mimickers as effective as the one of vanadium compounds. However, this type of activity has been observed and its causes studied. Thus, it has been found that treatment with tungstate restores the activity of key enzymes of carbohydrate metabolism in the liver of diabetic rats, which leads to an increase in the levels of glucose 6-phosphate and glycogen. Tungstate not only has effects on liver cells; it is also able to increase the lipoprotein lipase activity in adipose cells from streptozocin-diabetic rats to similar levels to those of healthy animals. This enzyme enables the cells to use the fatty acids that are transported by chylomicrons or VLDL (very low density lipoproteins) in the blood. Tungstate treatment also restored hepatic lipase activity. These data indicate that tungstate was also able to normalize lipoprotein metabolism in streptozocin diabetic rats.

In summary, the present invention solves the above-mentioned problem of having an appropriate insulin-mimicker drug for the oral treatment of diabetes mellitus, by providing a pharmaceutical composition comprising an effective amount of a compound of tungsten (VI) with a pharmaceutically acceptable chemical moiety, or a hydrate thereof, in combination with a pharmaceutically acceptable carrier.

In the context of this invention, the term "a compound formed by tungsten (VI) and a pharmaceutically acceptable chemical moiety" is intended to include any chemical entity formed by one or several tungsten atoms in its 6+ oxidation state (that is not toxic at therapeutical dose) attached to a chemical structure that is pharmaceutically acceptable by itself. The cation $W^{6+}$ has never been observed isolated, and it is always accompanied with a chemical moiety partially formed by a coordination sphere around the atom of W(VI). The coordination sphere can be formed by inorganic ligands (oxide, hydroxide, peroxide, etc) as, for example, in the case of the tungstate anion (coordination sphere formed by four oxide ions), or in the case of peroxytungstates (coordination sphere formed by mixtures of oxide and peroxide ions). The coordination sphere can also be formed by organic ligands which are molecules or ions attached to W(VI) atom through O, S or N atoms belonging to different pharmaceutically acceptable organic compounds (e.g. pharmaceutically acceptable alcohols, thiols, carboxylic acids, amines, aminoacids, N-containing heterocycles, etc). Mixed inorganic/organic coordination spheres are also possible. When the structure formed by the W(VI) atom and its coordination sphere is not neutral, the term "chemical moiety" also includes any pharmaceutically aceptable ionic species which makes neutral the whole tungsten (VI) compound. For example, the tungstate anion is always accompanied by a cation (e.g. sodium, potassium, magnesium, calcium) to form a neutral tungstate salt. Tungstate ion gives rise to a series of isopolytungstates (paratungstates, metatungstates, etc) which differ in the degree of aggregation; their use is also contemplated in this invention. Hydrates of tungsten (VI) compounds are common (e.g. the dihydrate of sodium tungstate), and their use is also considered part of this invention.

In a preferred embodiment, the tungsten (VI) compound in the pharmaceutical composition of this invention is a salt of tungstate or of a isopolytungstate, with a pharmaceutically acceptable cationic moiety. The salts of tungstate are especially preferred. Also preferred are the cationic moieties selected from the group of cations: sodium, potassium, magnesium and calcium. The most preferred tungsten (VI) compound is sodium tungstate, especially in the form of the dihydrate. The latter is commercially available.

Part of this invention is also a method of lowering blood sugar in a mammal comprising the oral administration of an effective amount of the above-mentioned pharmaceutical composition according to the invention. In a preferred method, the tungsten (VI) compound is sodium tungstate dihydrate. Daily oral doses between 0.5 and 500 mg/kg are especially preferred, and those between 50 and 500 mg/kg are even more preferred.

In a specific embodiment of the above-mentioned method of treatment, the mammal is a human suffering from insulin-dependent diabetes mellitus (IDDM), or Type 1 diabetes. As illustrated in the accompanying Example 1 and Table 1, oral administration of tungstate is very effective, and non-toxic at effective doses, in an animal model of human IDDM, namely, the streptozocin treated adult rat. It has been found that oral administration of tungstate is able to normalize glycemia and glucose hepatic metabolism in this animal model of IDDM, without changing insulin levels either in healthy or in diabetic rats. It is worth noting that the normoglycemic effect of tungstate is not due to an increase in the serum insulin levels, since no detectable change in immunoreactive insulin levels is observed after tungstate treatment. We have also found that tungstate also normalizes physical parameters, such as liquid and food intake, although it has no positive effect on weight gain. Surprisingly, tungstate does not exert a hepatotoxic effect, since serum alanine aminotransferase activity is reduced, and only a slight increase in aspartate aminotransferase is observed in diabetic rats.

In another embodiment of the above-mentioned method of treatment, the mammal is a human suffering from non-insulin-dependent diabetes mellitus (NIDDM), or Type 2 diabetes. As illustrated in the accompanying Example 2, tungstate is effective, and non-toxic at effective doses, in an animal model of human NIDDM, namely, the rat treated neonatally with a low-dose of streptozocin.

Both in Table 1 and in FIG. 1, it is observed that the tungstate treatment of healthy rats has only a minor effect on the level of glucose, i.e. does not produce hypoglycemia. Furthermore, no hypoglycemic episodes has been observed in tungstate-treated diabetic rats. This means that accidental administration of tungstate to non-diabetics or overdoses of tungstate in diabetics do not present the hypoglycemia problem associated with insulin, which provides an extra advantage of tungstate treatment.

The sugar-lowering effect of tungstate is not limited to hepatic carbohydrate metabolism, is not restricted to the adult streptozocin-treated rat, and can also be observed in vitro within the range of concentrations found in the serum of tungstate-treated animals.

In summary, the present invention satisfactorily solves the therapeutical problem of providing an insulin-mimicker drug for the oral treatment of diabetes mellitus. Compared with the closest prior art, represented by the use of vanadium compounds, the use of tungstate involves the advantage of a similar high sugar-lowering activity together with and much lower oral toxicity at effective doses. Besides, the long term toxicity of tungstate is low, as required for a prolonged treatment of the chronic disease diabetes mellitus, both of type 1 and Type 2. Finally, overdoses of tungstate do not present the adverse effect of hypoglycemia.

BRIEF DESCRIPTION OF THE DRAWINGS

The results are, in part, set out graphically in the following figures.

DESCRIPTION OF THE PREFERRED EMBODIMENTS

Figure 1:
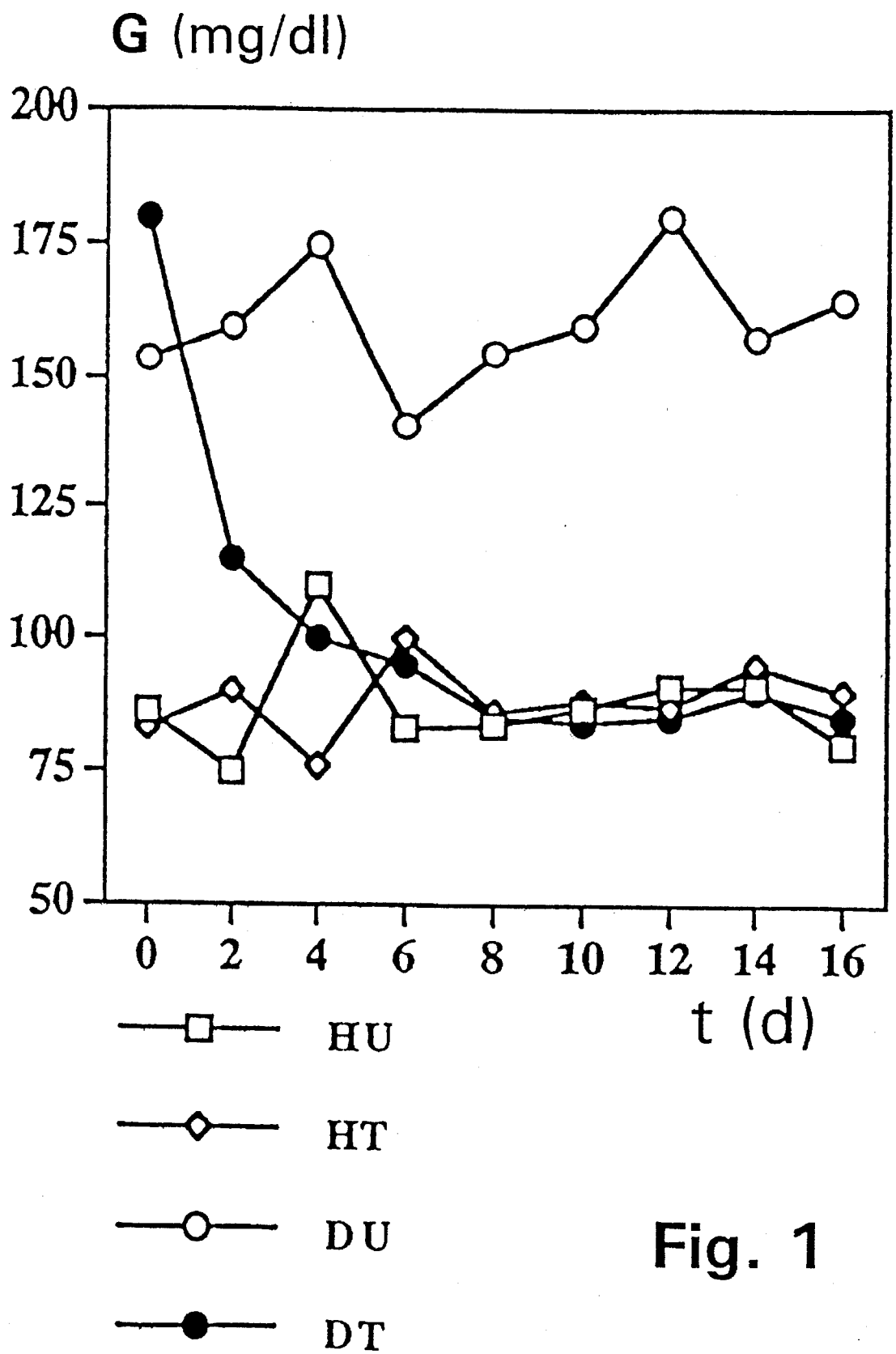
FIG. 1 is a graphical illustration of the variation of glycemia (G, mg/dl) with time (t, days) in an animal model of human NIDDM, along with a treatement with sodium tungstate. HU: Healthy Untreated; HT: Healthy Treated; DU: Diabetic Untreated; DT: Diabetic Treated.

The following examples illustrate the invention.

EXAMPLE 1: Insulin-mimicker Activity of Sodium Tungstate on a Model of Human IDDM (Type 1 Diabetes)

The effects of sodium tungstate on the highly hyperglycemic streptozocin-induced diabetic rats (a good animal model of human IDDM) were determined as follows:

Streptozotocin and sodium tungstate were from Sigma (St. Louis, Mo.). Enzymes and biochemical reagents were from either Boehringer Mannheim (Mannheim, Germany) or Sigma. All other chemicals were of analytical grade. Adult male Wistar (200 g) rats were kept under constant 12-hour light-dark cycle and were allowed to eat and drink ad libitum. When stated, diabetes was induced by a single endovenous injection of streptozocin (60 mg/kg body weight) in 0.9% NaCl with 100 mM sodium citrate buffer (pH 4.5). Diabetes was confirmed by determination of glucosuria and glycemia (Glucose and Glycemia strips. Boehringer Mannheim). Diabetic rats were used 5–7 days after streptozocin injection. At the beginning of the experiment, both diabetic and healthy animals were divided into two different groups. In the first group (untreated), rats received a solution of 0.9% NaCl as drinking water. The other animals (treated) were given a solution of 2 mg/ml of sodium tungstate in 0.9% NaCl. The treatment was carried out for 15 days. During this period, the fluid and food intake was measured each day between 4 and 6 p.m. At the end of the experiment, rats were anesthetized with diethylether and killed by decapitation between 9 and 11 a.m. Immediately, blood was collected to measure serum parameters. Meanwhile, livers were quickly sliced and fragments were either used immediately to measure enzyme activities or rapidly frozen in liquid $N_2$ for later determinations. Glycemia was determined by the hexokinase method (Glucoquant. Boehringer Mannheim). Determinations were adapted to a COBAS Bio autoanalyzer (Roche Biomedica. Basel, Switzerland). Serum insulin levels were determined by radioimmunoassay (Insik-5, Soren Biomedica. Saluggia, Italy).

Table 1 shows the variations of serum parameters due to tungstate administration. Results are expressed as the mean ± (standard errors) for the number of animals in parenthesis. It is observed that tungstate slightly increased serum glucose concentration in healthy rats. However, tungstate administration to diabetic rats counteracted the hyperglycemia observed in these animals, from 541 mg/dl (30.1 mM) to 195 mg/dl (10.8 mM). Insulin serum levels were also measured. Table 1 shows that tungstate administration did not change serum insulin levels either in healthy or in diabetic rats.

TABLE 1

| Effect of tungstate in a model of IDDM | | |
|---|---|---|
| | Glycemia (mg/dl) | Insulin (ng/ml) |
| Healthy rats | | |
| Untreated (11) | 169 ± 6 | 6.8 ± 1.9 |
| Treated (10) | 190 ± 3 | 6.1 ± 2.1 |
| Diabetic rats | | |
| Untreated (10) | 541 ± 33 | 1.3 ± 0.3 |
| Treated (10) | 195 ± 22 | 2.1 ± 0.7 |

EXAMPLE 2: Effect of Tungstate on a Model of Human NIDDM (Type 2 Diabetes)

To determine whether the effects of tungstate are of general application, experiments using an animal model which resembles human NIDDM were performed. This model is the rat treated neonatally with low doses of streptozocin, which develops slight hyperglycemia at 3–4 months. It was found that sodium tungstate treatment also normalizes glycemia in these animals, as shown in FIG. 1 for ten animals treated daily with 300–350 mg/kg (in the figure: HU=Healthy Untreated; HT=Healthy Treated; DU=Diabetic Untreated; DT=Diabetic Treated). All rats responded to the treatment and no macroscopic negative effect was observed. Furthermore, all animals survived the fifteen day treatment.

EXAMPLE 3: Other Insulin-like Effects of Tungstate in vitro

It was checked that tungstate is able to mimic insulin in cultured healthy rat hepatocytes. Tungstate at concentrations of 1 mM, 100 μM and 10 μM, was able to increase glycogen content to values similar to those values found for insulin.

EXAMPLE 4: Absence of Short-term Oral Toxicity

For the in vivo experiments, 200 g body weight male Wistar rats have been used. Different concentrations of sodium tungstate were administrated intragastrically, in order to calculate de $LD_{50}$ value, i.e., the concentration of sodium tungstate capable of killing the half of the animals, in ten days. Tungstate was dissolved with water and adjusted by clorhidric acid to pH 7.4. The single dose was administrated between 10–12 a.m. and the rats were allowed to eat to eat and drink ad libitum. The different doses used were the following ones:

— 464 mg/kg with five animals none of them died.
— 1000 mg/kg with nine animals only two of them died due to the treatment.
— 2150 mg/kg with ten animals and only one died.
— 2500 mg/kg with five animals and none of them died.
— 4640 mg/kg with ten animals and six died after the administration.
— 6500 mg/kg with five animals and three of them died.
— 8000 mg/kg with five animals and all of them died.

The $LD_{50}$ was calculated by the method of Horn, H. J. (Biometrics 1956, vol. 12, pp. 311–322). The value obtained was 3922 mg/kg of body weight, which is much smaller than the dose used for the treatment of diabetic rats (400 mg/kg), pointing out that the pharmacological effects were achieved at doses far from the toxic ranges.

EXAMPLE 5: Absence of Long-term Oral Toxicity

Figure 2:
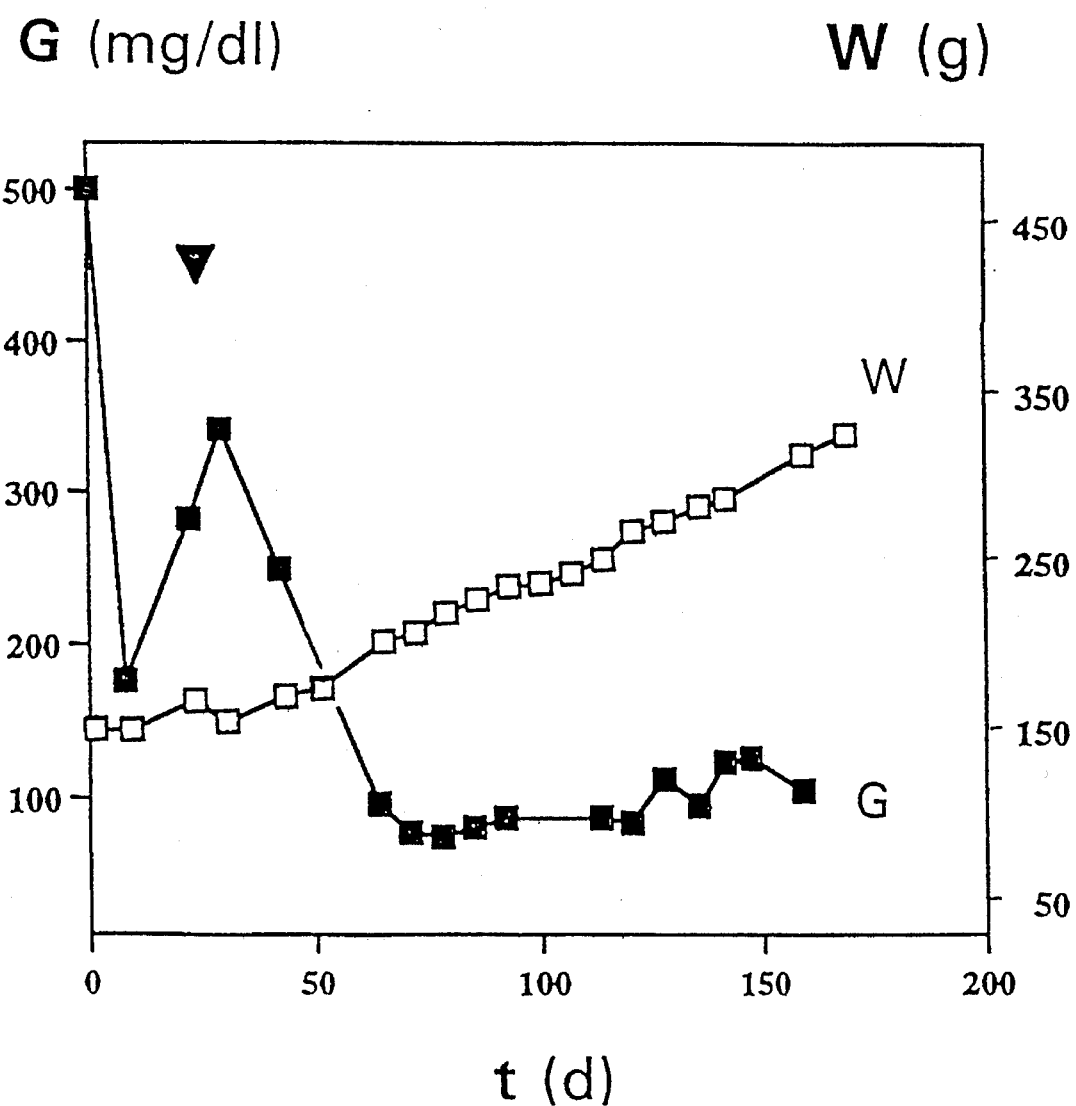
FIG. 2 is a graphical illustration of the evolution with time (t, days) of body weight (W, empty squares) and glycemia (G, filled squares) of a representative case, in one long term study of toxicology of tungstate in rats.

To assess the possible role of tungstate in the in vivo treatment of diabetes, a long-term experiment was performed. Sixteen rats were made diabetic by an intraperitoneal injection of streptozocin (70 mg/kg body weight). During two weeks, the animals received as drinking water a solution of 0.7 mg/ml of sodium tungstate, to get used to the tungstate taste. After this period, the dose was changed to a therapeutical one of 2 mg/ml. The animals were treated during 8 months, and no toxicological effects were observed in the healthy animals treated with tungstate. In the diabetic animals normalization of glycemia was observed more or less after two weeks of tungstate administration, and this normalization was maintained during all the treatment. Treatment prevented the appearance of diabetic complications, i.e. cataract, in the diabetic animals. FIG. 2 shows the evolution of body weight (W, empty squares) and glycemia (G, filled squares) in one of the treated rats which can be considered representative. The black triangle marks the beggining of the terapeutical treatment.

EXAMPLE 6: Absence of Toxicity in Animal Cells

The cytotoxic effects of tungstate were checked in primary cultured rat hepatocytes. The hepatocytes were isolated by collagenase digestion. Four rats were used to perform these experiments, after the hepatocytes were allowed to attach to the collagen-coated dishes and differentiate, the cells were incubated for 24 hours with different doses of tungstate (0.01, 0.1 and 1 mM). The toxicity of tungstate was evaluated by the release of a cytosolic enzyme to the extracellular medium, since when the cells die their intracellular content is released. The cytosolic enzyme activity measured was lactate dehydrogenase (LDH). The activity of this enzyme was determined by spectrophotometric assays with commercially available kits (Boehringher Mannheim) in a Cobas-Bio autoanalizer. One unit of LDH activity is the amount of enzyme catalyzing the formation of 1 μmol of NADH per minute at 30° C. The reaction catalyzed by LDH is:

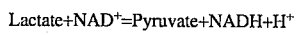

$$Lactate+NAD^+=Pyruvate+NADH+H^+$$

After the incubation with different doses of tungstate, an increase in LDH release was observed at 1 mM dose after 24 hours of incubation.

The mitochondrial function was analyzed in rat hepatocytes, this test is based on the reduction of yellow tetrazolium salts to an insoluble blue compound due to the activity of the mitochondrial enzyme succinate dehydrogenase. The test was performed after 24 hours of incubation with sodium tungstate. The cytotoxic indexes, $IC_{10}$ and $IC_{50}$, were calculated mathematically form the dose-response curves. These indexes indicate the theoretical concentration of tungstate which induces some toxic effects on the 10 or 50% of the cells, respectively. For rat hepatocytes, four rats were used and the cells were incubated with different doses of sodium tungstate between 0.26–2 mM to calculate the IC values, which were: $IC_{10}=0.6$ mM and $IC_{50}=1,2$ mM.

EXAMPLE 7: Absence of Toxicity in Human Cells

Human muscle cultures were initiated from satellite cells of muscle biopsies of two patients. Aneural-muscle cultures were established in a monolayer according to the explant-preexplantation technique. In primary cultured human muscle cells, the toxicity of tungstate was evaluated by cytosolic enzymes releasing to the extracellular medium, since when the cells died their intracellular content is released. Two cytosolic enzymes' activities were measured: lactate dehydrogenase (LDH) and creatine kinase (CK). Creatine kinase and lactate dehydrogenase activities were determined by spectrophotometric assays with commercially available kits (Boehringer Mannheim) in a Cobas-Bio autoanalizer. One unit of LDH activity is the amount of enzyme catalyzing the formation of 1 μmol of NADH per minute at 30° C. The reaction catalyzed by LDH is:

Lactate+NAD⁺=Pyruvate+NADH+H⁺

One unit of CK activity is the amount of enzyme catalyzing the formation of 1 μmol of ATP per minute at 25° C. The reaction catalyzed by CK is:

Creatinphosphate+ADP=Creatine+ATP

The culture medium was supplemented by different concentrations of sodium tungstate (0.01, 0.1, 0.5 and 1 mM), and only at the highest dose (1 mM) an increase in LDH and CK release was observed, after two days of incubation. At lower doses no increase in the release of these enzymes was detected, even when the cells were maintained with sodium tungstate for 15 days. Therefore, tungstate at doses of 0.5 mM or below is not toxic for human muscle cells.

The mitochondrial function was also analyzed in human hepatocytes, this test is based on the reduction of yellow tetrazolium salts to an insoluble blue compound due to the activity of the mitochondrial enzyme succinate dehydrogenase. The test was performed after 24 hours of incubation with sodium tungstate. The cytotoxic indexes, $IC_{10}$ and $IC_{50}$, were calculated as mentioned before, and two liver biopsies were analyzed, with doses of tungstate between 0.26–6 mM. The values obtained were higher than in rats: $IC_{10}=1$ mM and $IC_{50}=3$ mM; so in order to produce the same effect in human hepatocytes than in rat hepatocytes a higher concentration of tungstate is needed. Therefore tungstate is less toxic in human liver cells than in rat liver cells.

While the invention has been illustrated and described as embodied in tungsten (VI) compositions for oral treatment of diabetes mellitus, it is not intended to be limited to the details shown, since various modifications and structural changes may be made without departing from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of lowering blood sugar in a mammal comprising administering orally to said mammal an effective amount of a pharmaceutical composition, said pharmaceutical composition comprising an effective amount of a compound formed by tungsten (VI) and a pharmaceutically acceptable chemical moiety, or of a hydrate of said compound, in combination with a pharmaceutically acceptable excipient.

2. A method of lowering blood sugar in a mammal comprising administering orally to said mammal an effective amount of a pharmaceutical composition, said pharmaceutical composition comprising an effective amount of a compound consisting of a tungsten (VI) salt including a pharmaceutically acceptable cationic moiety and an anion selected from the group consisting of tungstate and isopolytungstates, or of a hydrate of said compound, in combination with a pharmaceutically acceptable excipient.

3. A method of lowering blood sugar in a mammal comprising administering orally to said mammal an effective amount of a pharmaceutical composition, said pharmaceutical composition comprising an effective amount of a compound consisting of a tungsten (VI) salt including a pharmaceutically acceptable cationic moiety and a tungstate anion, or of a hydrate of said compound, in combination with a pharmaceutically acceptable excipient.

4. A method of lowering blood sugar in a mammal comprising administering orally to said mammal an effective amount of a pharmaceutical composition, said pharmaceutical composition comprising an effective amount of a compound consisting of a tungsten (VI) salt including a pharmaceutically acceptable cationic moiety selected from the group consisting of sodium, potassium, magnesium and calcium and an anion selected from the group consisting of tungstate and isopolytungstates, or of a hydrate of said compound, in combination with a pharmaceutically acceptable excipient.

5. A method of lowering blood sugar in a mammal comprising administering orally to said mammal an effective amount of sodium tungstate or its dihydrate, in combination with a pharmaceutically acceptable excipient.

6. The method according to claim 5, wherein said sodium tungstate dihydrate is administered orally at a daily dose between 0.5 and 500 mg/kg.

7. The method according to claim 6, wherein the daily dose is between 50 and 500 mg/kg.

8. A method of treating insulin-dependent diabetes mellitus in a human comprising administering orally an effective amount of a compound formed by tungsten (VI) and a pharmaceutically acceptable chemical moiety, or of a hydrate of said compound, in combination with a pharmaceutically acceptable excipient, to said human.

9. The method as defined in claim 8, wherein the compound of tungsten (VI) is a salt comprising a pharmaceutically acceptable cationic moiety and an anion selected from the group consisting of tungstate and isopolytungstates.

10. The method as defined in claim 9, wherein said anion is said tungstate.

11. The method as defined in claim 9, wherein the cationic moiety is selected from the group consisting of sodium, potassium, magnesium and calcium cations.

12. The method as defined in claim 8, wherein the compound of tungsten (VI) is sodium tungstate and said hydrate is sodium tungstate dihydrate.

13. A method of treating noninsulin-dependent diabetes mellitus in a human comprising administering orally an effective amount of a compound formed by tungsten (VI) and a pharmaceutically acceptable chemical moiety, or of a hydrate of said compound, in combination with a pharmaceutically acceptable excipient, to said human.

14. The method as defined in claim 13, wherein the compound of tungsten (VI) is a salt comprising a pharmaceutically acceptable cationic moiety and an anion selected from the group consisting of tungstate and isopolytungstates.

15. The method as defined in claim 14, wherein said anion is said tungstate.

16. The method as defined in claim 14, wherein the cationic moiety is selected from the group consisting of sodium, potassium, magnesium and calcium cations.

17. The method as defined in claim 13, wherein the compound of tungsten (VI) is sodium tungstate and said hydrate is sodium tungstate dihydrate.

* * * * *